United States Patent
Kumari

(10) Patent No.: US 11,554,084 B2
(45) Date of Patent: Jan. 17, 2023

(54) COMPOSITIONS INCORPORATING AVOBENZONE-CALIX[8]-PO3H2 COMPLEX

(71) Applicant: University of Cincinnati, Cincinnati, OH (US)

(72) Inventor: Harshita Kumari, Loveland, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 17/535,970

(22) Filed: Nov. 26, 2021

(65) Prior Publication Data

US 2022/0160598 A1 May 26, 2022

Related U.S. Application Data

(60) Provisional application No. 63/118,151, filed on Nov. 25, 2020.

(51) Int. Cl.
   *A61K 8/35* (2006.01)
   *A61Q 17/04* (2006.01)
   *A61K 8/55* (2006.01)

(52) U.S. Cl.
   CPC .................. *A61K 8/35* (2013.01); *A61K 8/55* (2013.01); *A61Q 17/04* (2013.01); *A61K 2800/52* (2013.01); *A61K 2800/95* (2013.01)

(58) Field of Classification Search
   None
   See application file for complete search history.

(56) References Cited

PUBLICATIONS

Harshita Kumari et al., Investigating partitioning of free versus macrocycle bound guest into model POPC lipid bilayer, 2020, Royal Society of Chemistry, vol. 10, pp. 15148-15153 (Year: 2020).*

* cited by examiner

*Primary Examiner* — Nannette Holloman
(74) *Attorney, Agent, or Firm* — Brent M. Peebles

(57) ABSTRACT

A novel composition is disclosed comprising the complex avobenzone-calix[8]-$PO_3H_2$. In another embodiment, the present invention is a sunscreen composition comprising the complex avobenzone-calix[8]-$PO_3H_2$ and a cosmetically acceptable carrier.

8 Claims, 7 Drawing Sheets

COMPOSITIONS INCORPORATING AVOBENZONE-CALIX[8]-PO3H2 COMPLEX

CROSS REFERENCE TO RELATED APPLICATIONS

This application claims priority to U.S. Provisional Application Ser. No. 63/118,151, filed Nov. 25, 2020, which application is hereby incorporated by reference in its entirety.

TECHNICAL FIELD

The present invention relates to sunscreen actives.

BACKGROUND OF THE INVENTION

Supramolecular chemistry is transitioning from synthesizing unusable host-guest complexes to designing and developing molecular machines. Stoddart used molecules on the nanometric scale as switches in electronic devices and linear motormolecules in nanoelectromechanical systems. Investigating molecular movements and controlling them will define the next decade of supramolecular chemistry. The present invention involves the mechanism of penetration of a novel supramolecular host—guest complex across lipid bilayers/biomembranes, which is potentially useful to control UV radiation exposure, a potent cause of skin cancer.

The prevalence of malignant melanoma, despite the extensive use of sunscreens, is a global concern. UVA and UVB penetration across the epidermis leads to the generation of reactive oxidative species, DNA/protein/lipid damage and activation of varying signal transduction pathways that compromises the skin's defense systems. The use of sunscreens is continuously on the rise; however, the toxic effect of some organic sunscreens on coral reefs and challenges with formulation of inorganic sunscreen agents, such as, zinc oxide and titanium dioxide, has limited the number of available molecules that provide effective UV protection. Therefore, a need still exists for novel molecules that provide effective UV protection.

SUMMARY OF THE INVENTION

In one embodiment, the present invention is a composition comprising the complex avobenzone-calix[8]-$PO_3H_2$. In another embodiment, the present invention is a sunscreen composition comprising the complex avobenzone-calix[8]-$PO_3H_2$ and a cosmetically acceptable carrier. In one embodiment, the complex avobenzone-calix[8]-$PO_3H_2$ comprises from about 0.5 to about 10 weight percent of the sunscreen composition. In another embodiment, the sunscreen composition also includes one or more film formers. In one embodiment, the sunscreen composition also includes one or more emulsifiers. In another embodiment, the sunscreen composition also includes one or more silicone oils.

In one embodiment, the sunscreen composition is in the form of a lotion, cream, gel, or spray. In another embodiment, the cosmetically acceptable carrier comprises water.

DETAILED DESCRIPTION OF THE INVENTION

Figure 1A:
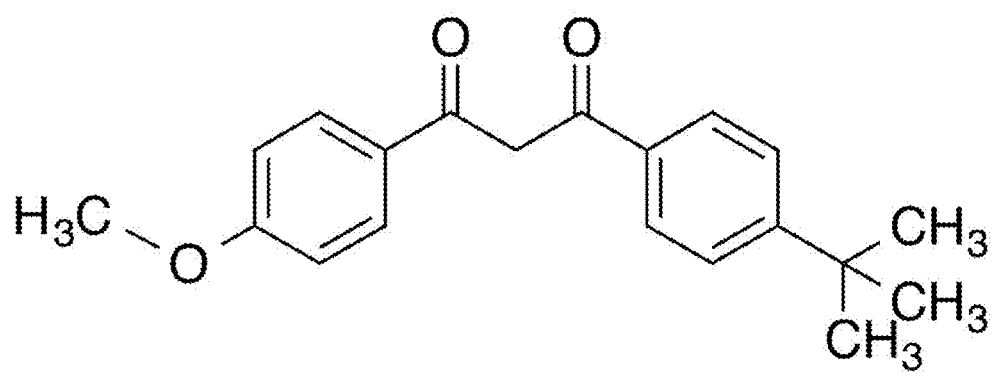
FIG. 1A is an illustration of the chemical structure of avobenzone.

The details of one or more embodiments of the disclosed subject matter are set forth in this document. Modifications to embodiments described in this document, and other embodiments, will be evident to those of ordinary skill in the art after a study of the information provided herein.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The compositions and methods of the present disclosure can comprise, consist of, or consist essentially of the essential elements and limitations of the disclosure described herein, as well as any additional or optional ingredients, components, or limitations described herein or otherwise useful.

All percentages, parts and ratios herein are based upon the total weight of the compositions of the present disclosure, unless otherwise indicated.

As used herein, the term "about," when referring to a value or to an amount of mass, weight, time, volume, pH, size, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

"Cosmetically acceptable" means that the item in question is compatible with a keratinous substrate such as skin and hair. For example, a "cosmetically acceptable carrier" means a carrier that is compatible with a keratinous substrate such as skin and hair.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The photo-stability of sunscreen actives, the toxicological impacts of photo-degradation products and controlling skin penetration are three of the major challenges for current sunscreen products. Sunscreens such as oxybenzone/benzophenone-3 are emerging as environmental contaminants, impacting coral reefs. Some sunscreens have contaminated humans as well. They have been detected in human urine in 97% of the population. Thus, skin penetration across deeper layers (dermis) is a major concern with organic photoactives. Although macromolecular quantitative estimation of skin penetration of sunscreen is possible via radiolabelled $^{14}C$ tape stripping assays on human/pig skin, a nanometric molecular level understanding is still lacking. The present invention involves an organic active (avobenzone, FIG. 1A) complexed with a macrocycle (FIG. 1B). The interaction of this complex with model lipid bilayer membranes is examined to determine its potential impact and/or restrain its pathway across the bilayer membrane.

Figure 1B:
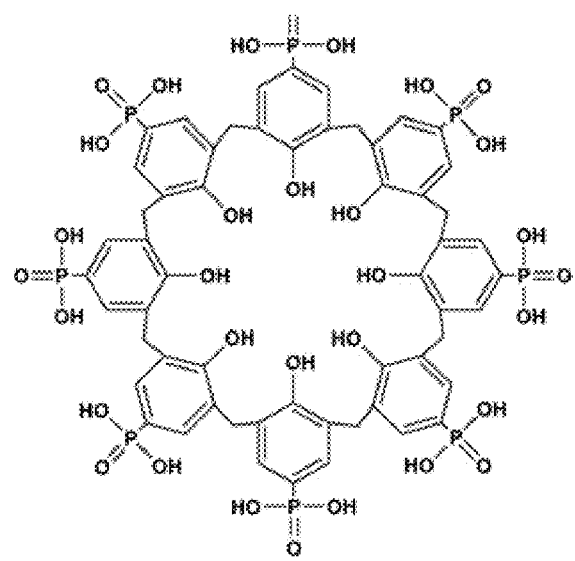
FIG. 1B is an illustration of the chemical structure of p-phosphonated calix [8]arene.

In one embodiment of the present invention, p-phosphonated calix[8]arene (calix [8]-$PO_3H_2$) (FIG. 1B) is used as the host molecule and avobenzone as the sunscreen agent (FIG. 1A). Calixarenes are cyclic oligomers of several phenolic units connected with methylene bridges. While the base molecule is sparingly soluble in water, it has been modified for the present invention with functional groups, such as, phosphonate, sulphonate or amine to induce aqueous solubility. In addition, the cavity size can be modulated to accommodate a suitably sized guest. Rat and human cell toxicology studies on calix[8]-$PO_3H_2$ revealed its non-toxic behavior that renders it a useful biomedical macrocycle for potential application as a nanocarrier. Complexation of calix[8]-$PO_3H_2$ with avobenzone was chosen for three reasons: (a) water solubility of the macrocycle; (b) large internal cavity and upper rim H-bonding functionality of the host and (c) non-toxic behavior towards rat and human cell lines.

Avobenzone (1-(4-methoxyphenyl)-3-(4-tertbutylphenyl)-propane-1,3-dione) also known as Parsol 1789 is a broad-spectrum sunscreen agent. Its ability to absorb both UVA and UVB radiations makes it one of the more useful sunscreen agents that prevents photodamage of skin. However, once exposed to sun, avobenzone offers only 30 minutes of photoprotection. Hence, it is formulated with photostabilizers, such as octocrylene, which is a known endocrine disrupter and releases free radicals. Experimental and theoretical studies suggest that the chelated enol form is the ground state. Upon UV irradiation in polar nonprotic solvents, the enol form converts to the keto tautomer. The present invention has found a rather inert macrocycle that can provide a confined environment for photostability and/or controlled penetration across bilayer. The present invention involves the interaction of free versus macrocycle-complexed avobenzone with an artificial bilayer.

The Avobenzone:Calix[8]-$PO_3H_2$ Complex

A stock solution of 100 mM avobenzone was made in dimethylsulfoxide (DMSO) and 100 mM calix[8]-$PO_3H_2$ was made in water. Equimolar quantities of avobenzone: calix[8]-$PO_3H_2$ (1:1) are mixed together to obtain complex and allowed to equilibrate for 24 hours.

The interaction of avobenzone and calix[8]-$PO_3H_2$ was tested with single-membrane POPC (1-palmitoyl-2-oleoyl-sn-glycero-3-phosphocholine) tethered lipid bilayer membranes (tBLMs). Solvent-immersed tBLMs allowed for a characterization of the membrane before and after addition of avobenzone and calix[8]-$PO_3H_2$ from solution, thus mimicking the encounter of those substances by the membrane in the body. This differentiates tBLMs from conventionally used stacked lipid bilayer model systems in air. The chemical structure of the glycerophospholipid POPC consists of a zwitterionic phosphatidylcholine headgroup linked to a glycerol, which is ester-bound to two fatty acid groups—palmitic acid (C16:0) and oleic acid (C18:1). This fatty acid composition mimics that of phospholipids mainly found in the eukaryotic cell membrane, including keratinocytes. In addition to phospholipids, native eukaryotic membranes also contain glycolipids, sterols and various proteins, which are not included in the current simplified model system.

Using a POPC model membrane constitutes the first step in establishing more complex SC lipid membrane model systems. Specifically, in the cornification process, keratinocytes, which are living cells containing phospholipid bilayer membranes, a nucleus and cytoplasm, are transformed to corneocytes via apoptosis. Consequently, the digestion of the nucleus and the loss of the cytoplasm and all intracellular organelles occur, whereas the cell membrane is replaced by the cornified cell envelope (CE). The CE consists of cross-linked structural proteins (e.g. loricrin, involucrin), which are also covalently linked to ceramides on the exterior surface providing a hydrophobic interface between the CE and the intercellular lipid lamellae. The simplified biomimetic lipid bilayer model enables the investigation of its fundamental interaction with molecules of interest between the molecular and the micrometer scale using neutron reflectometry (NR). Because neutrons are uncharged and highly penetrating particles that have wavelengths comparable to molecular sizes and inter-molecular distances, neutrons are an ideal probe for characterizing the structure and dynamics of complex materials such as lipid bilayers. Moreover, neutrons interact with hydrogen and deuterium differently allowing one to use of the scattering contrast between $H_2O$ and $D_2O$ to investigate hydrogen-rich biological membranes. There are three different neutron scattering techniques commonly applied for different membrane models: (a) neutron diffraction for stacked bilayers (b) small angle neutron scattering for vesicles and bicelles, and (c) NR for single bilayers such as the POPC used herein.

NR is a flexible tool in structural biology due to its ability to discern the biomolecular architectures of lipid membranes and membrane-associated proteins without destroying the sample. It allows to mimic biological processes and to measure their structural responses. However, it does require specific deuteration to resolve individual components of interest.

Cosmetically Acceptable Carrier

In one embodiment, the avobenzone:calix[8]-PO$_3$H$_2$ complex of the present invention is useful as an ingredient of sunscreen compositions. In one embodiment, the complex avobenzone-calix[8]-PO$_3$H$_2$ comprises from about 0.5 to about 10 weight percent of the sunscreen composition. In another embodiment, the complex avobenzone-calix[8]-PO$_3$H$_2$ comprises from about 1 to about 5 weight percent of the sunscreen composition. The sunscreen compositions include a cosmetically acceptable carrier. The phrase "cosmetically acceptable" means that the material is compatible with skin and hair. For example, "cosmetically acceptable carrier" means a carrier that is compatible with skin and hair, and is acceptable for application to the body.

The cosmetically acceptable carrier may include, for example, water and/or water soluble solvents. Non-limiting examples of cosmetically acceptable carriers include glycerin, C1-4 alcohols, organic solvents, fatty alcohols, fatty ethers, fatty esters, polyols, glycols, vegetable oils, mineral oils, liposomes, laminar lipid materials, water, or any combinations thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

In some instances, cosmetically acceptable carriers may comprise water, a mixture of water and at least one cosmetically acceptable organic solvent, or at least one cosmetically acceptable organic solvent. Additionally, cosmetically acceptable carriers may be or may include ethanol, a glycol ether, for example, dipropylene glycol n-butyl ether, isododecane, mineral oil, propylene glycol, pentylene glycol, hexylene glycol, glycerol, and mixtures thereof.

The total amount of cosmetically acceptable carrier can vary, but in some instances may be about 50 to about 95 wt. %, based on the total weight of the sunscreen composition. In some instances, the total amount of cosmetically acceptable carrier is about 55 to about 95 wt. %, about 60 to about 95 wt. %, about 70 to about 95 wt. %, about 75 to about 95 wt. %, about 50 to about 90 wt. %, about 60 to about 90 wt. %, about 70 to about 90 wt. %, or about 75 to about 90 wt. %, based on the total weight of the sunscreen composition.

Film Formers

Film-formers may be incorporated into the sunscreen compositions to ensure even coverage of UV filters and can be used to render the composition water resistant. The film former is typically a hydrophobic material that imparts film forming and/or waterproofing characteristics. One such agent is polyethylene, which is available from New Phase Technologies as Performalene® 400, a polyethylene having a molecular weight of 400. Another suitable film former is polyethylene 2000 (molecular weight of 2000), which is available from New Phase Technologies as Performalene®. Yet, another suitable film former is synthetic wax, also available from New Phase Technologies as Performa® V-825. Other typical film-formers include acrylates/acrylamide copolymer, acrylates copolymer, acrylates/C12-C22 alkylmethacrylate copolymer, polyethylene, waxes, VP/dimethiconylacrylate/polycarbamylpolyglycol ester, butylated PVP, PVP/hexadecene copolymer, octadecene/MA copolymer, PVP/eicosene copolymer, tricontanyl PVP, *Brassica Campestris/Aleuritis* Fordi Oil copolymer, decamethyl cyclopentasiloxane (and) trimethylsiloxysilicate, and mixtures thereof. In some cases, the film former is acrylates/C12-C22 alkylmethacrylate copolymer sold under the tradename Allianz OPT® by ISP.

The total amount of film forming in the sunscreen compositions, if present, may vary but is typically about 0.1 to about 40 wt. %, based on the total weight of the sunscreen composition. In some instances, the total amount of film formers may be about 0.1 to about 30 wt. %, about 0.1 to about 20 wt. %, about 0.1 to about 10 wt. %, about 1 to about 40 wt. %, about 1 to about 30 wt. %, about 1 to about 20 wt. %, or about 1 to about 10 wt. %, based on the total weight of the sunscreen composition.

Emulsifiers

The sunscreen compositions may optionally include at least one emulsifier such as an amphoteric, anionic, cationic or nonionic emulsifier, used alone or as a mixture, and optionally a co-emulsifier. Emulsifiers are most often used when the sunscreen composition is in the form of an emulsion. The emulsifiers are chosen in an appropriate manner according to the emulsion to be obtained (W/O or O/W).

The total amount of emulsifiers in the sunscreen compositions, if present, may vary but are typically about 0.1 to about 30 wt. %, based on the total weight of the sunscreen composition. In some instances, the total amount of emulsifiers is about 0.1 to about 20 wt. %, about 0.1 to about 15 wt. %, about 0.1 to about 10 wt. %, about 0.5 to about 30 wt. %, about 0.5 to about 20 wt. %, about 0.5 to about 15 wt. %, about 0.5 to about 10 wt. %, about 1 to about 30 wt. %, about 1 to about 20 wt. %, about 1 to about 15 wt. %, about 1 to about 10 wt. %, or about 5 to about 5 wt. %, based on the total weight of the sunscreen composition.

Silicone Oils

The sunscreen compositions may optionally include one or more silicone oils. Non-limiting examples of silicone oils include dimethicone, cyclomethicone, polysilicone-11, phenyl trimethicone, trimethylsilylamodimethicone, and stearoxytrimethylsilane. In some cases, the cosmetic composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates.

The total amount of silicone oils in the sunscreen compositions, if present, can vary but is typically about 0.1 to about 40 wt. %, based on the total weight of the sunscreen composition. In some cases, the total amount of silicone oils in the sunscreen composition may be about 0.1 to about 30 wt. %, about 0.1 to about 20 wt. %, about 0.1 to about 10 wt. %, about 1 to about 40 wt. %, about 1 to about 30 wt. %, about 1 to about 20 wt. %, about 1 to about 10 wt. %, about 5 to about 40 wt. %, about 5 to about 30 wt. %, about 5 to about 20 wt. %, or about 5 to about 15 wt. %, based on the total weight of the sunscreen composition.

Forms

The form of the sunscreen compositions is not limited. For example, the sunscreen compositions may be in the form of a cream, a gel, a paste, a lotion, a rinse, a foam, an emulsion, a spray, etc. The sunscreen compositions may be prepared according to techniques that are well known to those skilled in the art, in particular those intended for the preparation of emulsions of oil-in-water or water-in-oil type. They may be in particular in the form of a simple or complex emulsion (O/W, W/O, O/W/O or W/O/W emulsion) such as a cream or a milk, in the form of a gel or a cream-gel, or in the form of a lotion.

EXAMPLES

Example 1

Neutron Reflectometry (NR) experiments were conducted with hydrogenated and deuterated POPC bilayers. Both data sets were simultaneously analyzed to obtain one structural model. NR measurements were performed with the CGD-Magik reflectometer at the NIST Center for Neutron Research (NCNR). Reflectivity curves were recorded for momentum transfer values $0.01 \leq q_z \leq 0.25$ Å$^{-1}$. For each measurement, adequate counting statistics were obtained after 5-7 h. The NCNR fluids cell allows for in situ solvent exchange; therefore, subsequent measurements were performed on the same sample area. The entire flow cell was maintained at room temperature (RT). Solvent exchange was accomplished by rinsing ~10 ml of water through the cell (volume ~1.3 ml) using a syringe.

Example 2

A set of NR experiments was conducted with a hydrogenated POPC bilayer and another identical set of experiments with a deuterated POPC-$d_{31}$ bilayer. After measurement of the as-prepared bilayer in H$_2$O and D$_2$O, avobenzone was added to the sample cell at a concentration of 100 μM dissolved in H$_2$O and D$_2$O. NR measurements were conducted while the bilayer was in contact with either solution. The sample was measured again after rinsing with H$_2$O and D$_2$O, respectively. Data for both bilayers were co-refined sharing conserved model parameters across data sets, in particular those associated with the volume profile of avobenzone. The co-refinement of data from two lipid bilayers with differently labelled hydrocarbon chains significantly boosted the resolution of the avobenzone profile, in this region. An identical set of measurements were performed with a 100 μM complex of 1:1 avobenzone:calix[8]-PO$_3$H$_2$ instead of pure avobenzone.

Example 3

1D-component volume occupancy (CVO) profiles along the lipid bilayer normal were obtained. Bilayer fit parameters were the hydrocarbon thickness for each bilayer sub-section, the bilayer completeness, and the thickness of the sub-membrane space. One roughness parameter was applied to all distributions. The thin layer of native silicon oxide was modelled by a single distribution with individual roughness and thickness parameters. Hermite splines defined by control points that were on average 15 Å apart were used to model the CVO profiles of avobenzone and calix[8]-PO$_3$H$_2$. The number of control points was iteratively refined during model optimization for each CVO profile. Fit parameters associated with each control point were a volume occupancy, a deviation from equidistant separation, and (for the CVO profile of the complex) a nSLD (neutron scattering length density) value between those of avobenzone and calix[8]-PO$_3$H$_2$. Such a variable nSLD per control point allowed us to separate individual CVO profiles for avobenzone (average nSLD $\rho=1.37\times10^{-6}$ Å$^{-2}$) and calix[8]-PO$_3$H$_2$ ($\rho=2.73\times10^{-6}$ Å$^{-2}$). The exchange of labile protons in isotopically different buffers affects the nSLD of molecular components and was taken into account during data analysis. Optimization of model parameters was performed using the ga_refl and Refl1D software packages developed at the NCNR. A Monte Carlo Markov chain-based global optimizer was used to determine fit parameter confidence limits.

NR Measurement Results

Figure 2A:
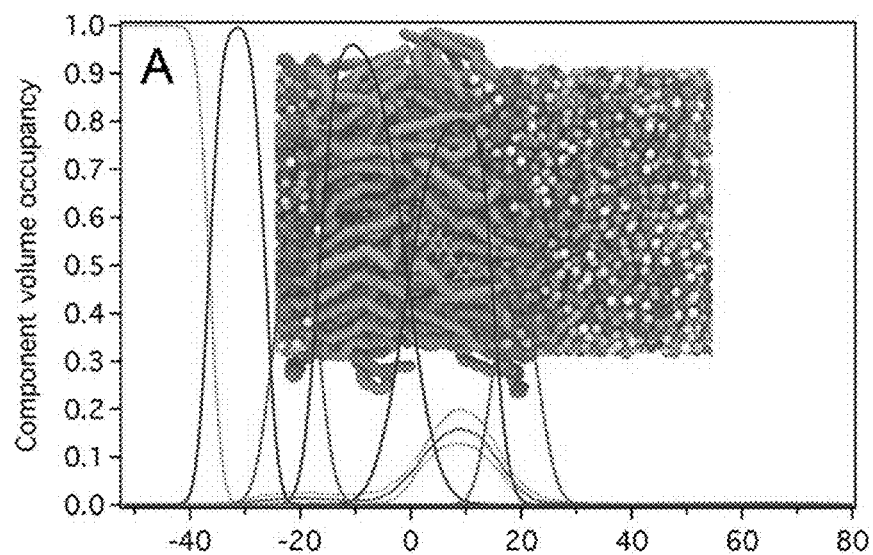
FIG. 2A is a graph showing an NR-derived CVO profile of a hydrogenated 1-palmitoyl-2-oleoyl-sn-glycero-3-phosphocholine (POPC) bilayer while incubating 100 mM avobenzone.
Figure 2B:
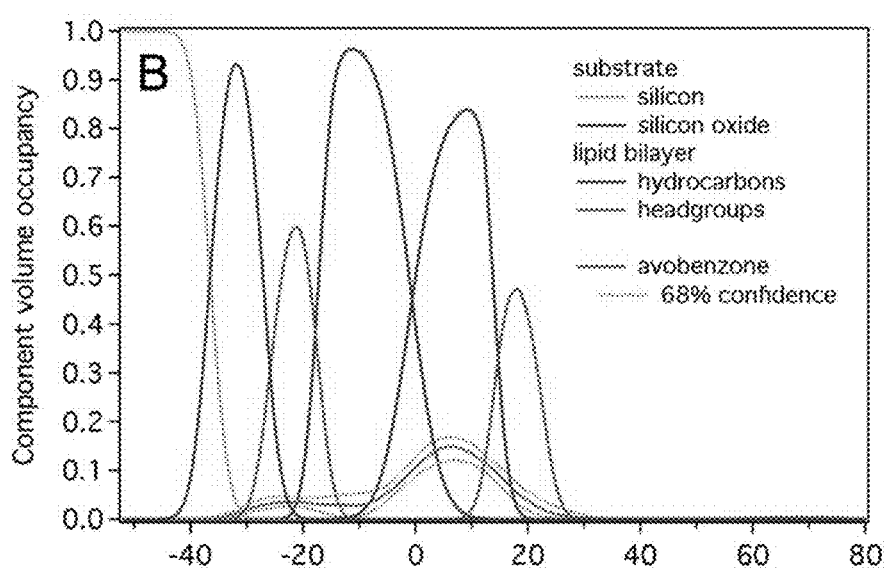
FIG. 2B is a graph showing an NR-derived CVO profile of a hydrogenated POPC bilayer post-rinse.

Results for NR measurements with avobenzone without calix [8] are shown in FIGS. 2A and 2B and Table 1. For FIGS. 2A-2D, 68% confidence limits are shown for avobenzone and calix[8]-PO$_3$H$_2$ profiles. A complementary set of POPC-$d_{31}$ bilayers were identically prepared and measured, and simultaneously analyzed with the respective data sets collected on the hydrogenated POPC bilayers (data not shown).

TABLE 1

|  | 100 μM incubation | | Rinse | |
|---|---|---|---|---|
|  | POPC-$d_{31}$ | POPC | POPC-$d_{31}$ | POPC |
| Substrate | | | | |
| Thickness silicon oxide (Å) | 10.2 ± 0.6 | 8.5 ± 0.5 | 9.4 ± 1.0 | 8.9 ± 1.0 |
| Substrate roughness, σ (Å) | | 2.4 ± 0.3 | | 3 ± 1 |
| Bilayer | | | | |
| Thickness sub-membrane space (Å) | 0.4 ± 0.4 | 0.5 ± 0.4 | 0.4 ± 0.4 | 0.8 ± 0.3 |
| Substrate-proximal hydrocarbon thickness (as-prepared) (Å) | 15.7 ± 0.6 | 16.7 ± 0.5 | 15.9 ± 0.9 | 17.9 ± 0.5 |
| Substrate-distal hydrocarbon thickness (as-prepared) (Å) | 14.5 ± 0.5 | 13.3 ± 0.5 | 13.7 ± 0.9 | 12.6 ± 0.5 |
| Thickness change per leaflet after adding avobenzone | +0.5 ± 0.2 | +0.6 ± 0.2 | +0.7 ± 0.3 | +0.4 ± 0.2 |
| Bilayer completeness, as-prepared | 1.00 ± 0.01 | 1.00 ± 0.01 | 1.00 ± 0.01 | 1.00 ± 0.01 |
| Bilayer completeness, with avobenzone | 0.99 ± 0.01 | 1.00 ± 0.01 | 1.00 ± 0.01 | 1.00 ± 0.01 |
| Avobenzone | | | | |

TABLE 1-continued

| | 100 μM incubation | | Rinse | |
|---|---|---|---|---|
| | POPC-$d_{31}$ | POPC | POPC-$d_{31}$ | POPC |
| Peak of avobenzone CVO from bilayer center (Å) | 10 ± 3 | | 7 ± 3 | |
| Surface volume density (Å$^3$/Å$^2$) | 3.0 ± 0.5 | | 3.8 ± 0.4 | |
| | ~1 avobenzone per 2.7 lipids in outer leaflet | | ~1 avobenzone per 2.1 lipids in outer leaflet | |

The substrate-supported POPC and POPC-$d_{31}$ lipid bilayers were complete (surface coverage 1.00±0.01) and had total hydrocarbon thicknesses of 30±1 Å, which is ~3 Å larger than those determined for stacked lipid bilayer membranes and vesicles. Avobenzone is observed interacting with the lipid bilayer at the hydrocarbon/headgroup interface of the substrate-distal lipid leaflet or solvent-side region without penetrating the bilayer to the substrate-proximal leaflet. The observed surface volume density of avobenzone is 3.0±0.5 Å$^3$/Å$^2$ during bilayer incubation and 3.8±0.4 Å$^3$/Å$^2$ after solvent rinse, showing a stable bilayer-association with 1 avobenzone molecule per ~2.7 lipid molecules. Adding avobenzone does not affect the structural integrity of the lipid bilayer as the bilayer completeness remains at 100±1%. A substantial thickening of the lipid bilayer of ~0.5 Å per leaflet upon avobenzone addition is observed.

Figure 2C:
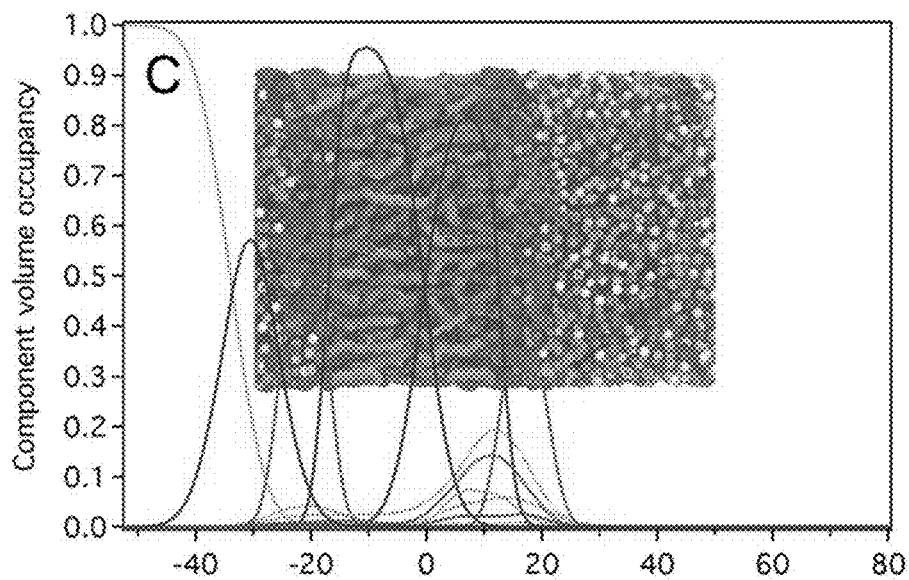
FIG. 2C is a graph showing an NR-derived CVO profile of a second hydrogenated POPC bilayer while incubating 100 mM avobenzone and calix[8]-$PO_3H_2$.
Figure 2D:
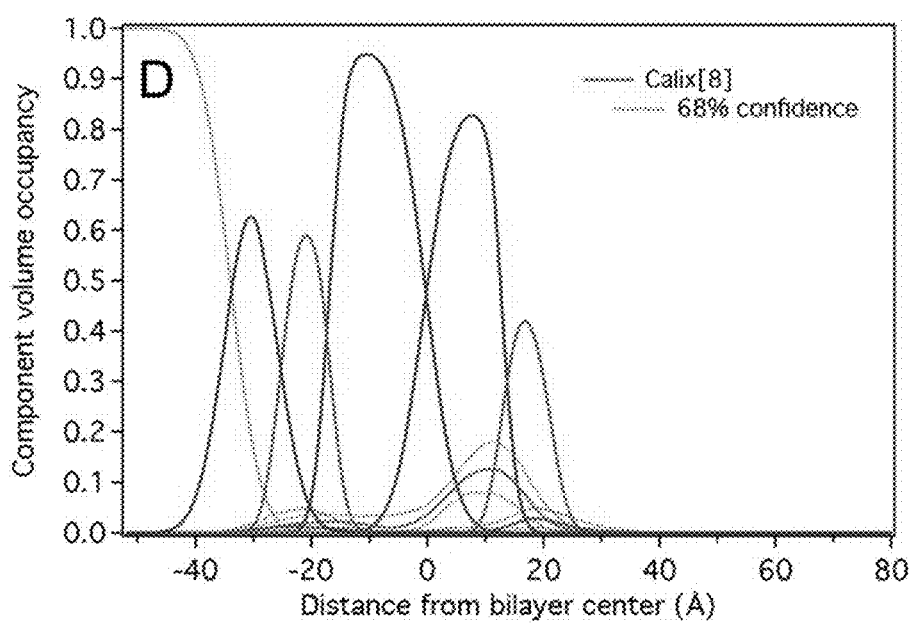
FIG. 2D is a graph showing an NR-derived CVO profile of a second hydrogenated POPC bilayer post-rinse.

FIGS. 2C, 2D and Table 2 show NR results for the measurements involving the avobenzone:calix[8]-PO$_3$H$_2$ complex.

that of calix[8]-PO$_3$H$_2$, the molar ratio of calix[8]-PO$_3$H$_2$ to avobenzone at the membrane is substantially less than 1. This indicates a dissociation of avobenzone from calix [8]-PO$_3$H$_2$ before or upon bilayer interaction, which is consistent with the weak hydrogen bonding of avobenzone to calix[8]-PO$_3$H$_2$ at the upper rim. Post-rinsing, both the amount of bilayer-associated avobenzone and macrocycle remains unchanged. The lipid bilayer remains structurally intact throughout the experiment.

Example 4

Molecular dynamics simulations were conducted using the GROMACS/4.2.1 suite of programs. The system was set up by conjoining an equilibrated box containing a POPC lipid bilayer with two equilibrated water boxes. The combined configuration forms a rectangular prism of dimensions 6 nm×6 nm×12 nm. Forcefields used were CHARMM27 for the lipids, the TIP3P water model, and the CHARMM

TABLE 2

| | 100 μM incubation | | Rinse | |
|---|---|---|---|---|
| | POPC-$d_{31}$ | POPC | POPC-$d_{31}$ | POPC |
| Substrate | | | | |
| Thickness silicon oxide (Å) | 11 ± 1 | 7 ± 1 | 11 ± 1 | 7 ± 1 |
| Substrate roughness, σ (Å) | 4.6 ± 0.5 | | 4.8 ± 0.5 | |
| Bilayer | | | | |
| Thickness sub-membrane space (Å) | 1 ± 2 | 1.0 ± 0.6 | 2 ± 2 | 1 ± 1 |
| Substrate-proximal hydrocarbon thickness (as-prepared) (Å) | 13 ± 1 | 16 ± 1 | 13 ± 1 | 16 ± 1 |
| Substrate-distal hydrocarbon thickness (as-prepared) (Å) | 14 ± 1 | 13 ± 1 | 14 ± 1 | 13 ± 1 |
| Thickness change per leaflet after adding avobenzone: Calix[8] | +0.1 ± 0.2 | −0.3 ± 0.1 | +0.4 ± 0.3 | −0.4 ± 0.1 |
| Bilayer completeness, as-prepared | 1.00 ± 0.01 | 1.00 ± 0.01 | 1.00 ± 0.01 | 1.00 ± 0.01 |
| Bilayer completeness, with avobenzone: Calix[8] | 0.99 ± 0.01 | 0.99 ± 0.01 | 0.99 ± 0.01 | 0.99 ± 0.01 |
| Avobenzone: Calix[8] | | | | |
| Peak of avobenzone CVO from bilayer center (Å) | 11 ± 3 | | 10 ± 3 | |
| Surface volume density of avobenzone (Å$^3$/Å$^2$) | 2.3 ± 0.6 | | 2.5 ± 0.4 | |
| | ~1 avobenzone per 3.0 lipids in outer leaflet | | ~1 avobenzone per 2.8 lipids in outer leaflet | |
| Surface volume density of Calix[8] (Å$^3$/Å$^2$) | 0.7 ± 0.5 (not significant) | | 0.6 ± 0.5 (not significant) | |

The POPC and POPC-$d_{31}$ lipid bilayers were structurally identical to those prepared for the avobenzone measurements, albeit the hydrocarbon region was on average 2 Å thinner, and therefore closer to literature values. While a comparable surface volume density of bilayer-associated avobenzone of 2.3±0.6 Å$^3$/Å$^2$ (1 avobenzone per ~3.1 lipid molecules) was observed, the density of calix[8]-PO$_3$H$_2$ arene was barely significant with 0.7±0.6 Å$^3$/Å$^2$. Since the solvent-excluded volume of avobenzone is roughly a third of general forcefield for avobenzone and calix[8]-PO$_3$H$_2$. Initial positions for the avobenzone molecule and the avobenzone:calix[8]-PO$_3$H$_2$ complex were chosen to be 2 nm from the lipid surface, to prevent premature interaction with the POPC surface. The initial configuration of the avobenzone: calix[8]-PO$_3$H$_2$ complex was chosen following an unrestrained MD equilibration of the two species in an aqueous environment, this resulting structure represents a low energy configuration of the two molecules interacting in a "bowlsolute" conformation. The systems were equilibrated using the NVT ensemble followed by the NPT ensemble for 1 ns and 5 ns, respectively, using the Nose-Hoover thermostat and the Parrinello-Rahman barostat. After equilibration, umbrella pulling simulations were conducted in the negative z-direction to generate configuration windows for the potential-of-mean-force (PMF) calculations. 300 configurations were extracted from the pull trajectories to ensure proper sampling. Each simulation window was reequilibrated for a short period 0.5 ns, then production runs were conducted. During production, the center of mass of the "pulled" molecule(s) (avobenzone or avobenzone-calix[8]-$PO_3H_2$) are restrained, but rotation around their center of mass and molecule flexing is allowed to prevent unrealistic configurations. Each production run was sampled for 6 ns with a 2 fs timestep and coupling times of 2 and 4 fs for the thermostat and barostat respectively. Samples from each production window were analyzed using the GROMACS implementation of the weighted histogram analysis (gmx WHAM). The PMFs were shifted so that zero energy corresponds to the solutes in bulk water.

Figure 3A:
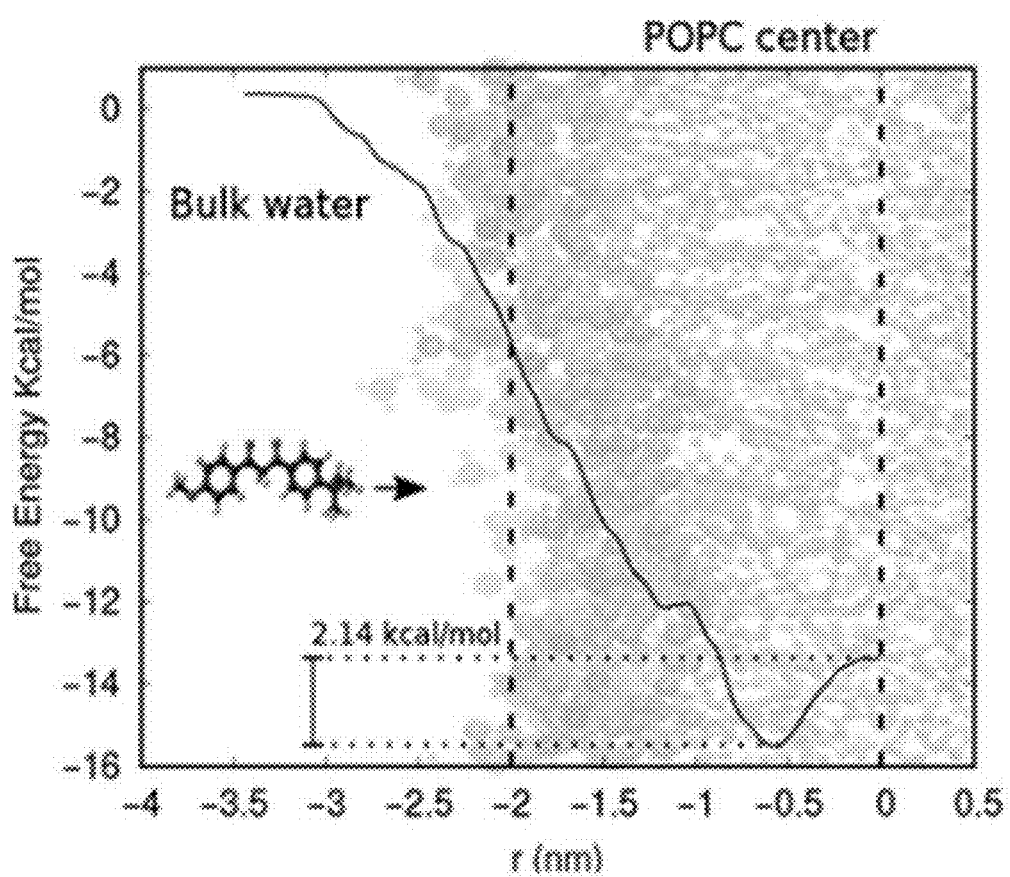
FIG. 3A is a graph showing the free energy change as a function of the distance of avobenzone from the POPC lipid bilayer's center.
Figure 3B:
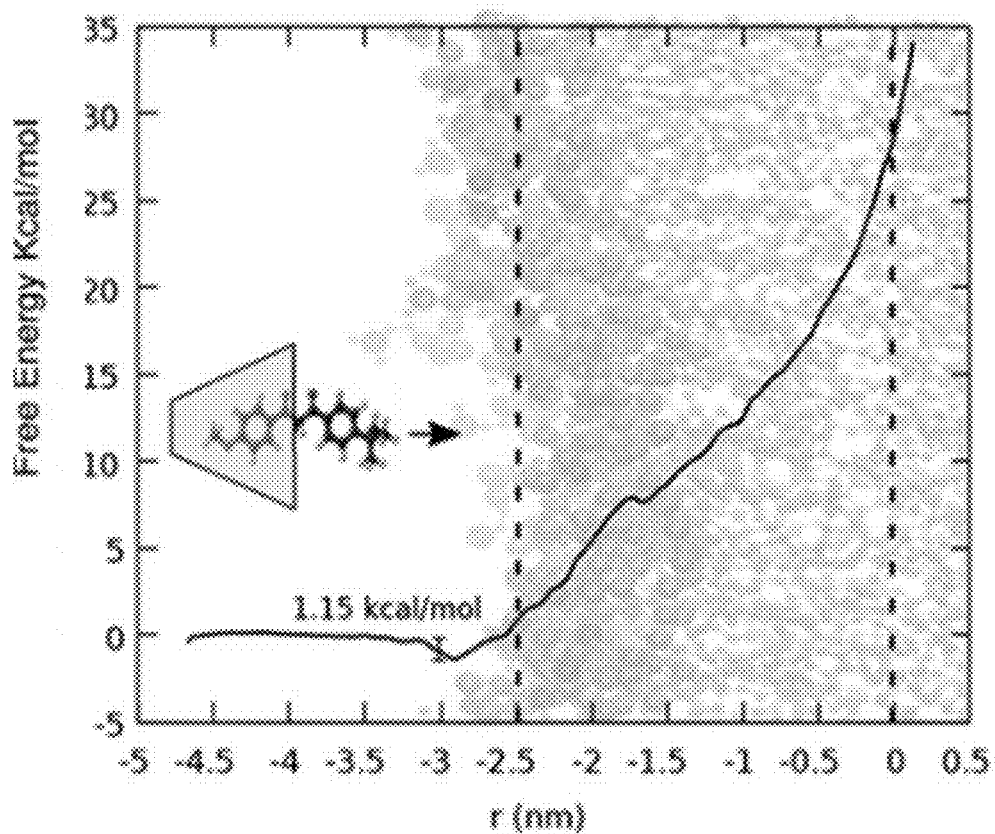
FIG. 3B is a graph showing the free energy change as the avobenzone:calix[8]-$PO_3H_2$ complex approaches the bilayer.

FIG. 3A shows the free energy change as a function of the distance of avobenzone from the POPC lipid bilayer's centre of mass. A negative change in free energy is observed as avobenzone partitions into the lipid bilayer. The local minimum of the free energy profile is located at ~0.7 nm, which indicates that avobenzone after partitioning into the membrane will settle near this position and which is in agreement with the peak of the CVO profiles of avobenzone obtained from the NR experiments (FIGS. 2A-2D; Tables 1 and 2). FIG. 3B shows the free energy change as the avobenzone:calix[8]-$PO_3H_2$ complex approaches the bilayer. In contrast to the result with avobenzone only, a shallow local minimum is located at the surface of the bilayer (3 nm from the bilayer center). Moving into membrane the free energy rises sharply not exhibiting an energetically favorable configuration. This indicates the difficulty the avobenzone:calix[8] complex faces attempting to permeate even the outer layers of the bilayer. The free energy continues to rise after crossing the center of mass of the POPC lipid bilayer further indicating that the forced permeation in our simulations is disrupting the bilayer structure. Error bars in FIGS. 3A and 3B are omitted for clarity, but standard deviation of each point on the curve is estimated to be between 0.3 and 0.5 kcal $mol^{-1}$ using the bootstrap analysis method. The local free energy minimum of ~1.5 kcal $mol^{-1}$ is too shallow to stably bind a significant amount of the complex at a solution concentration of 100 μM. Simulations therefore agree with the absence of a significant amount of calix[8]-$PO_3H_2$ detected in NR.

Combined NR and simulation results reveal the interaction of avobenzone with the bulk solvent-side region (outer leaflet) of a POPC membrane. Un-complexed avobenzone is shown to strongly penetrate into the membrane and associate with 5 lipid molecules; however, in the presence of calix[8]-$PO_3H_2$ the complex encounters a large free energy barrier to membrane entry. These energetically favorable positions lead to the penetration of a single avobenzone to the first hydrophobic region of the POPC lipid bilayer, while the avobenzone:calix[8]-$PO_3H_2$ complex instead enjoys an energetically favorable position at the surface of the bilayer. These preferred positions agree with the NR results showing calix[8]-$PO_3H_2$ accumulating at the lipid bilayer surface and avobenzone settling in the first hydrophobic region. The avobenzone by itself displays a 2.1 kcal $mol^{-1}$ energy well in the first inner leaflet, higher than the energy well of the avobenzone:calix[8]-$PO_3H_2$ complex at the lipid bilayer surface (1.2 kcal $mol^{-1}$). In addition, simulations have identified a free energy minimum for membrane-bound avobenzone 6 Å from the membrane center, inside the first hydrophobic region of the bilayer. This is in agreement with the experimentally determined peak positions of the avobenzone CVO profiles of 10±3 Å and 7±3 Å (Table 1). The free energy difference between membrane bound avobenzone and avobenzone at infinite dilution of −16 kcal $mol^{-1}$ estimates to an affinity in the nM range. This calculated value being lower than the experimental concentration of 100 mM may suggest that the overall free energy difference between bound and solvated states should be smaller than the calculated −16 kcal $mol^{-1}$ if the concentration in the simulated bulk phase matched that of the experiments. These results showcase the ability of the calix[8]-$PO_3H_2$ macrocycle to reduce the penetration of the avobenzone into a simple lipid bilayer, providing a useful way of anchoring targeted molecules to the surface of a membrane and reducing molecular permeation.

Figure 4A:
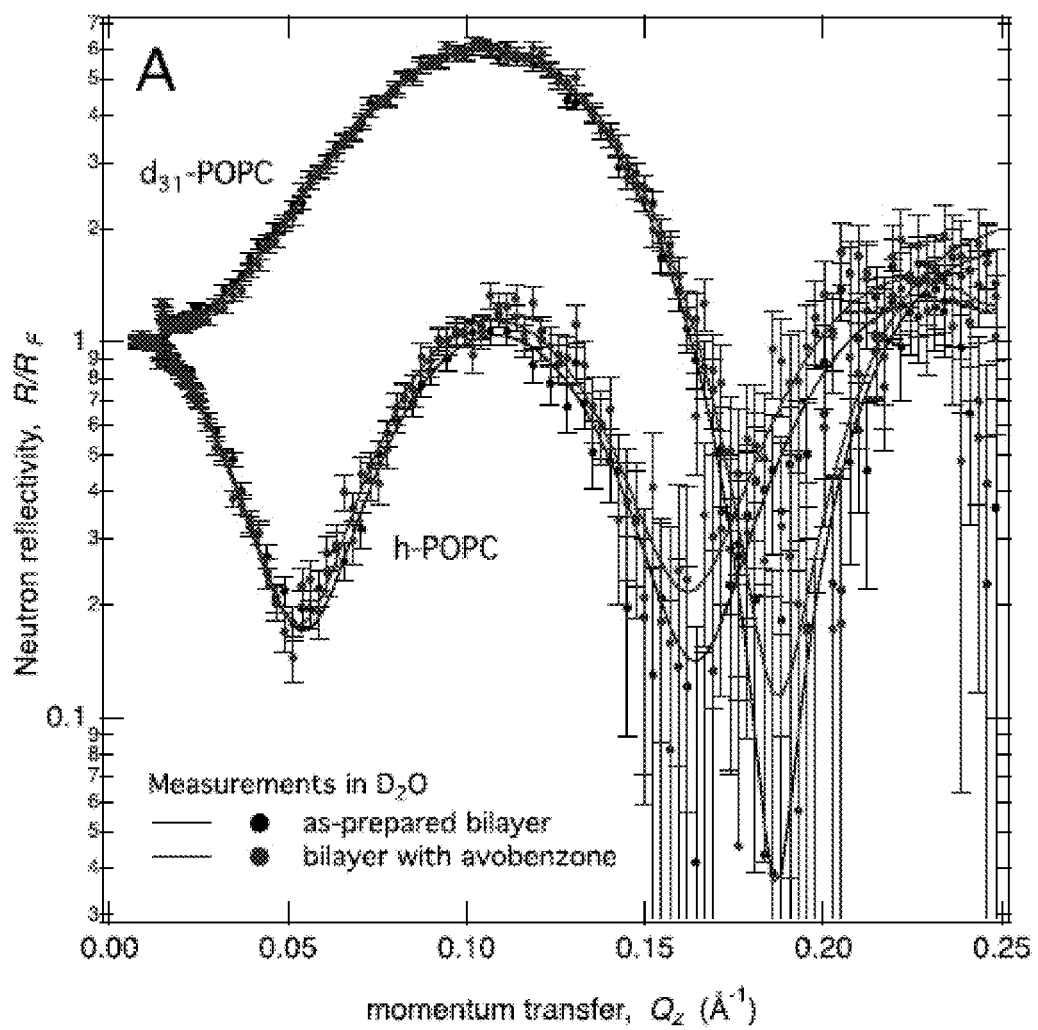
FIG. 4A is a graph showing fresnel-normalized neutron reflectivity curves for two independent measurements of a h-POPC and a $d_{31}$-POPC bilayer, as prepared and while incubating 100 μM avobenzone.
Figure 4B:
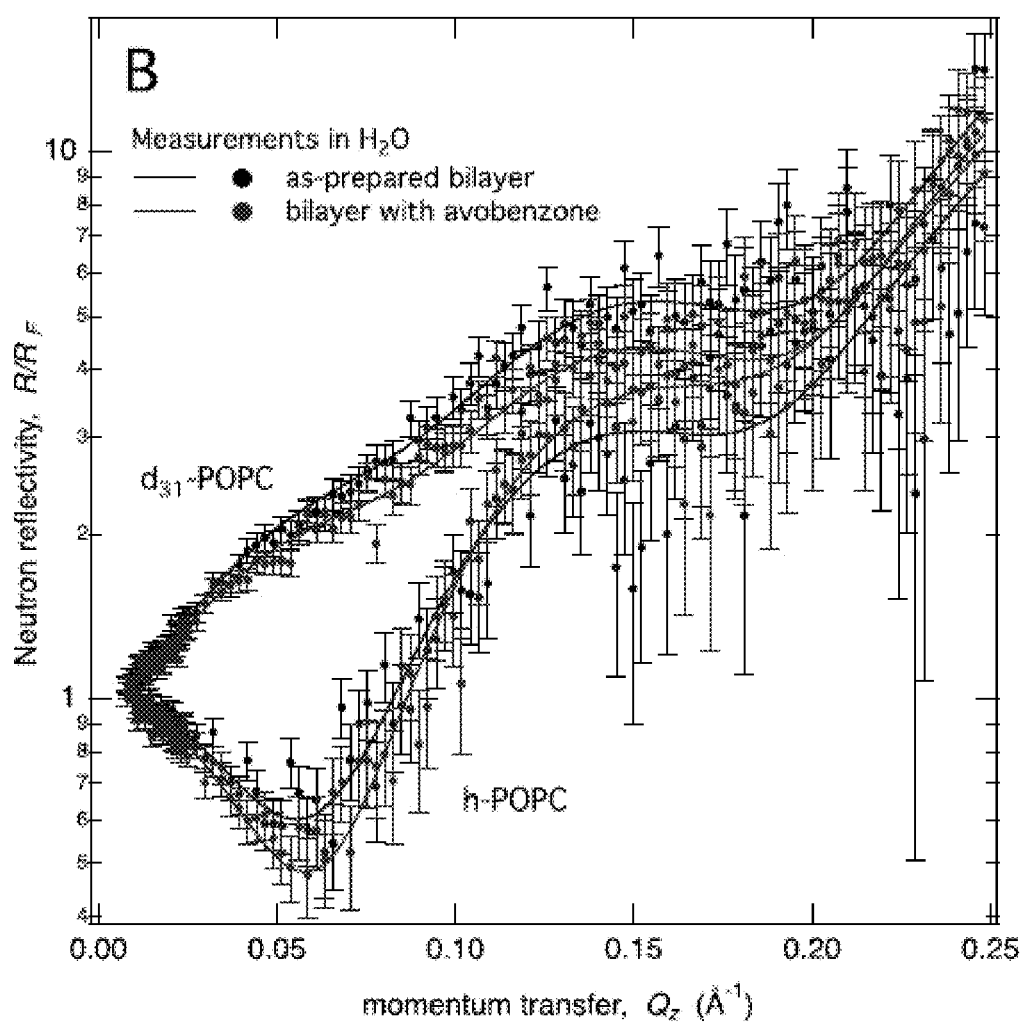
FIG. 4B is a graph showing fresnel-normalized neutron reflectivity curves for two independent measurements of a h-POPC and a $d_{31}$-POPC bilayer, as prepared and while incubating 100 μM avobenzone.

FIGS. 4A and 4B show fresnel-normalized neutron reflectivity curves for two independent measurements of a h-POPC and a $d_{31}$-POPC bilayer, as prepared and while incubating 100 μM avobenzone. Each condition was characterized using two isotopically distinct bulk solvents, $D_2O$ for FIG. 4A and $H_2O$ for FIG. 4B. Significant changes in the reflectivity were observed for most combinations of bilayer and bulk solvent upon addition of avobenzone. The entire set of eight reflectivity curves was analyzed simultaneously using one structural model. Combining two measurements with bilayers that differ in their lipid chain deuteration was important in resolving avobenzone in the lipid bilayer core. Qualitatively similar reflectivities were recorded after rinsing and for the complex of avobenzone and calix[8]-$PO_3H_2$ during incubation and after rinsing.

All documents cited are incorporated herein by reference; the citation of any document is not to be construed as an admission that it is prior art with respect to the present invention.

It is to be further understood that where descriptions of various embodiments use the term "comprising," and/or "including" those skilled in the art would understand that in some specific instances, an embodiment can be alternatively described using language "consisting essentially of" or "consisting of"

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed is:

1. A composition comprising the complex avobenzone-calix[8]-$PO_3H_2$.

2. A sunscreen composition comprising the complex avobenzone-calix[8]-$PO_3H_2$ and a cosmetically acceptable carrier.

3. The sunscreen composition of claim 2 wherein the complex avobenzone-calix[8]-$PO_3H_2$ comprises from about 0.5 to about 10 weight percent of the sunscreen composition.

4. The sunscreen composition of claim 2 further comprising one or more film formers.

5. The sunscreen composition of claim 2 further comprising one or more emulsifiers.

6. The sunscreen composition of claim 2 further comprising one or more silicone oils.

7. The sunscreen composition of claim 2 in the form of a lotion, cream, gel, or spray.

8. The sunscreen composition of claim 2, wherein the cosmetically acceptable carrier comprises water.

* * * * *